United States Patent
Pottala

(10) Patent No.: US 10,475,536 B2
(45) Date of Patent: Nov. 12, 2019

(54) METHOD OF DETERMINATION OF RISK OF 2 HOUR BLOOD GLUCOSE EQUAL TO OR GREATER THAN 140 MG/DL

(71) Applicant: True Health Diagnostics, LLC, Frisco, TX (US)

(72) Inventor: James Viktor Pottala, Sioux Falls, SD (US)

(73) Assignee: True Health IP LLC, Frisco, TX (US)

( * ) Notice: Subject to any disclaimer, the term of this patent is extended or adjusted under 35 U.S.C. 154(b) by 469 days.

(21) Appl. No.: 14/335,378

(22) Filed: Jul. 18, 2014

(65) Prior Publication Data

US 2015/0024422 A1    Jan. 22, 2015

Related U.S. Application Data

(60) Provisional application No. 61/847,922, filed on Jul. 18, 2013.

(51) Int. Cl.
| | | |
|---|---|---|
| *G16H 50/20* | (2018.01) | |
| *G01N 33/68* | (2006.01) | |
| *G16B 99/00* | (2019.01) | |
| *G16H 50/30* | (2018.01) | |

(52) U.S. Cl.
CPC ......... *G16H 50/20* (2018.01); *G01N 33/6893* (2013.01); *G16B 99/00* (2019.02); *G01N 2800/042* (2013.01); *G01N 2800/50* (2013.01); *G16H 50/30* (2018.01)

(58) Field of Classification Search
None
See application file for complete search history.

(56) References Cited

U.S. PATENT DOCUMENTS

| | | | |
|---|---|---|---|
| 2012/0208215 A1 | 8/2012 | Hu et al. | |
| 2013/0137632 A1 | 5/2013 | Pfuetzner et al. | |
| 2016/0357935 A1* | 12/2016 | Pottala | G06F 19/3431 |

FOREIGN PATENT DOCUMENTS

| | | | | |
|---|---|---|---|---|
| WO | WO 2008009869 A1 * | 1/2008 | ....... | G01N 33/56916 |
| WO | WO 2011059721 A1 * | 5/2011 | ............ | G01N 33/66 |
| WO | WO2014/074889 | 5/2014 | | |

OTHER PUBLICATIONS

Bhatnagar et al., "Assessment of insulin resistance using surrogate markers in patients of metabolic syndrome," Diabetes Metab Syndr 5(1):29-32 (Jan. 1, 2011).

Watkins et al., "Biomarker models as surrogates for the disposition index in the Insulin Resistance Atherosclerosis Study," Diabet Med 29(11):1399-406 (Nov. 2012).

* cited by examiner

*Primary Examiner* — Soren Harward
(74) *Attorney, Agent, or Firm* — Perkins Coie LLP

(57) ABSTRACT

This invention relates to methods for predicting likelihood of a subject having abnormal glucose tolerance based on analyzing a combination of three or more biomarkers relating to specific physiological processes. This invention also relates to methods of accessing insulin sensitivity in a subject based on analyzing a combination of three or more biomarkers relating to specific physiological processes. The method has a clinical utility in correct and quick assessment of a subject's glucose tolerance and risk of developing diabetes or cardio-diabetic conditions and comorbidities.

12 Claims, 6 Drawing Sheets

METHOD OF DETERMINATION OF RISK OF 2 HOUR BLOOD GLUCOSE EQUAL TO OR GREATER THAN 140 MG/DL

This application claims the benefit of priority of U.S. Provisional Patent Application Ser. No. 61/847,922, filed Jul. 18, 2013, which is hereby incorporated by reference in its entirety.

FIELD OF THE INVENTION

The invention relates to the field of clinical diagnostics. More specifically, the invention involves clinical testing of biomarkers to predict the likelihood of a subject having impaired glucose tolerance or insulin resistance.

BACKGROUND

Currently, a number of tests exist that can diagnose whether a patient has a normal glucose tolerance (NGT) or an impaired glucose tolerance (IGT). One test is to measure the blood glucose level at a 2-hour point of OGTT: elevated blood glucose above 140 mg/dL indicates abnormal glucose tolerance. Other tests that may indicate abnormal glucose tolerance include measuring levels of fasting blood glucose, insulin, pro-insulin, c-peptide, HbA1C, fructosamine, glycation gap, 1,5-Anhydroglucitol (1,5 AG), OGTT, "clamp-like index" (CLIX) scoring (an index obtained from plasma OGTT glucose and C-peptide levels and serum creatinine), homeostasis model assessment-estimated insulin resistance (HOMA IR) scoring, and immuno reactive insulin (IRI) scores based on combinations of alpha hydroxybutyrate (AHB), linoleoyl-GPC (L-GPC), and oleic acid weighted by insulin or body mass index (BMI). The above tests, used alone or in combination, can detect the presence of pre-diabetes (metabolic syndrome) and early insulin resistance in patients who are normoglycemic in fasting state.

The best current predictors of fasting normoglycemic patients who may be at risk of developing diabetes are OGTTs and CLIX scoring of OGTTs. Both techniques involve testing multiple analytes at multiple time-points, requiring the patient to have a blood sample drawn at baseline (fasting) and to drink a beverage containing a known quantity of glucose, and subsequently contacting patient blood samples and measuring the levels of various analytes (e.g. glucose, insulin, pro-insulin, c-peptide, creatinine) at fasting baseline and at various time intervals after dosing with the glucose load. Most OGTTs and CLIX scoring require a patient to remain in the doctor's office for 2 hours post dose, and most clinicians only test baseline samples and compare to the testing at the 2 hour time point, not the labor-intensive additional blood draws for 3-5 times during the 2-hour period necessary for the CLIX scoring, due to labor and cost constraints. Moreover, complicated and laborious mathematical calculations need to be performed in order to optimize detection of at-risk individuals with these techniques. Additionally, kidney function (approximated by blood creatinine levels/eGFR) needs to be accounted for with these techniques, requiring a further step.

Thus, there is a need in the art for diagnostic biomarkers and tests that can identify patients at risk of developing Type 2 diabetes as well as the risk of disease progression in patients with insulin resistance.

SUMMARY OF THE INVENTION

One aspect of the invention relates to a method for predicting likelihood of a subject having abnormal glucose tolerance. The method comprises: a) obtaining, from a biological sample in a subject, measured level of a combination of biomarkers relating to at least three of the following physiological processes: adipose tissue insulin resistance, pancreatic beta cell dysfunction and/or exhaustion, muscle and/or hepatic insulin resistance, functional enhancement of insulin secretion by beta cells, inhibition of beta cell function, adipokine function, total glycemic control, and inflammation; b) calculating a score based on the measured levels of the biomarkers, wherein the score calculation involves a mathematical transformation, and c) comparing the score to reference values from a population. An elevated score correlates with an increased likelihood of elevation of blood glucose to ≥140 mg/dL at 2 hours after oral glucose tolerance test and indicates that the subject has an increased likelihood of having abnormal glucose tolerance. A low score correlates with a decreased likelihood of elevation of blood glucose to ≥140 mg/dL at 2 hours post oral glucose tolerance test and indicates that the subject has a decreased likelihood of having abnormal glucose tolerance.

Another aspect of the invention relates to a method of accessing insulin sensitivity in a subject. The method comprises the step of obtaining, from a biological sample in a subject, measured levels of a combination of biomarkers relating to at least three of the following physiological processes: adipose tissue insulin resistance, pancreatic beta cell dysfunction and/or exhaustion, muscle and/or hepatic insulin resistance, functional enhancement of insulin secretion by beta cells, inhibition of beta cell function, adipokine function, total glycemic control, and inflammation isolated from a subject. The method further comprises comparing the measured levels of the biomarkers to glucose disposal reference levels of the biomarkers. A glucose disposal rate lower than the glucose disposal reference levels indicates an increased likelihood of early insulin resistance, and a glucose disposal rate higher than the glucose disposal reference levels indicates a decreased likelihood of early insulin resistance.

The embodiments of this invention provide a diagnostic tool to clinicians that enable the prediction of likelihood of impaired glucose tolerance as defined by a 2-hour OGTT blood glucose level of ≥140 mg/dL. An algorithm is used herein based on a combination of 3 or more specific classes of analytes, each with a distinct and different physiological role in the complex interplay of factors that determine normal or abnormal glucose tolerance. This algorithm has a clinical utility in identifying, in a single fasting sample, individuals who are highly likely to have an abnormally high 2-hour glucose if an OGTT were to be performed, and thus can serve as a proxy or replacement for the OGTT measurement. This algorithm also enables reclassification of NGT to IGT, and IGT to NGT, thus enabling correct assessment of glucose tolerance and risk of cardiodiabetic disease and comorbidities. The diagnostic tool therefore enables healthcare professionals to select treatment protocols for optimal therapeutic intervention and improved clinical outcomes.

DETAILED DESCRIPTION OF THE INVENTION

Figure 1:
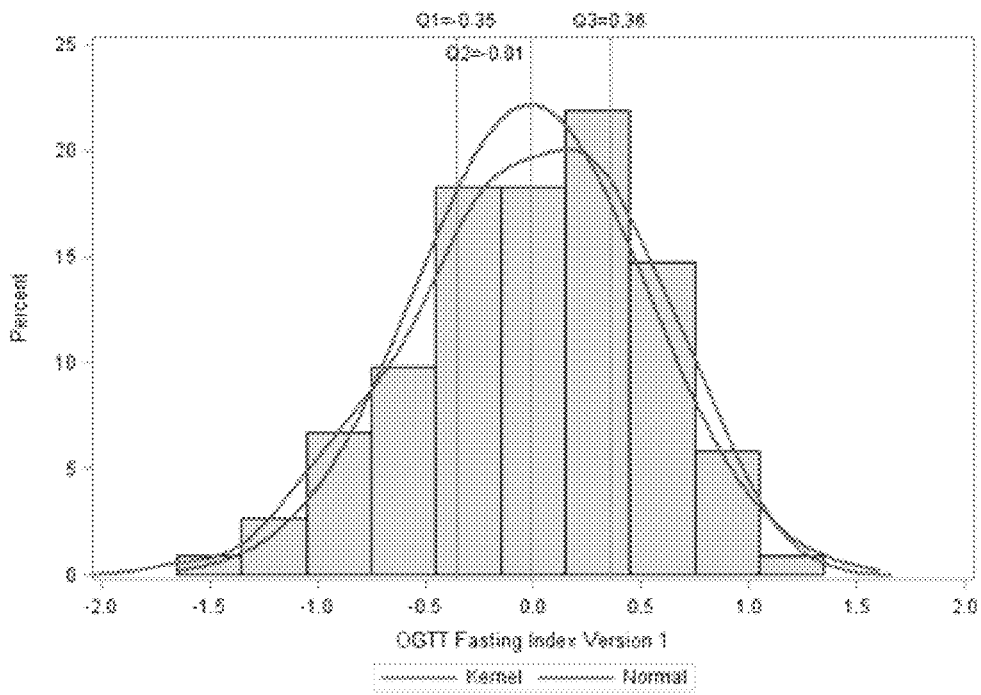
FIG. 1 is a graph showing the histogram of a OGTT fasting score distribution from patients of a population study using Version 1 of the equation. The vertical lines of Q1, Q2, and Q3 indicate the score cutoffs for the first quantile, the second quantile, and the third quantile, respectively. The line "kernel" represents the kernel density estimation, i.e., a non-parametric estimation of the probability density function of a random variable; and the line "normal" represents the best fit of the normal distribution.

One aspect of the invention relates to a method for predicting likelihood of a subject having abnormal glucose tolerance. The method comprises: a) obtaining, from a biological sample in a subject, measured level of a combination of biomarkers relating to at least three of the following physiological processes: adipose tissue insulin resistance, pancreatic beta cell dysfunction and/or exhaustion, muscle and/or hepatic insulin resistance, functional enhancement of insulin secretion by beta cells, inhibition of beta cell function, adipokine function, total glycemic control, and inflammation; b) calculating a score based on the measured levels of the biomarkers, wherein the score calculation involves a mathematical transformation, and c) comparing the score to reference values from a population. An elevated score correlates with an increased likelihood of elevation of blood glucose to ≥140 mg/dL at 2 hours after oral glucose tolerance test and indicates that the subject has an increased likelihood of having abnormal glucose tolerance. A low score correlates with a decreased likelihood of elevation of blood glucose to ≥140 mg/dL at 2 hours post oral glucose tolerance test and indicates that the subject has a decreased likelihood of having abnormal glucose tolerance.

Another aspect of the invention relates to a method of determining abnormal glucose tolerance in a subject. The method comprises predicting a glucose disposal rate in a subject by analyzing a biological sample from a subject to determine a level(s) of biomarkers relating to three or more physiological processes in the sample. The three or more physiological processes are selected from the group consisting of: adipose tissue insulin resistance, pancreatic beta cell dysfunction and/or exhaustion, muscle and/or hepatic insulin resistance, functional enhancement of insulin secretion by beta cells, inhibition of beta cell function, adipokine function, total glycemic control, and inflammation. The level(s) of the biomarkers in the sample is compared to glucose disposal reference levels of the biomarkers to determine insulin sensitivity in the subject.

Another aspect of the invention relates to a method of determining abnormal glucose tolerance in a subject. The method comprises predicting a glucose disposal rate in a subject by analyzing a biological sample from a subject to determine a level(s) of three or more biomarkers chosen from the group consisting of: total free fatty acids, ferritin, c-peptide, AHB, L-GPC, and adiponectin.

Another aspect of the invention relates to a method of determining abnormal glucose tolerance in a subject. The method comprises predicting a glucose disposal rate in a subject by analyzing a biological sample from a subject to determine a level(s) of three or more biomarkers comprising at least total free fatty acids, c-peptide, and adiponectin.

The method can involve multiple steps such as patient sampling, laboratory analysis, and mathematical transformation of data, so that appropriate therapeutic steps can be taken.

A biological sample can be obtained from a living subject to analyze the biomarkers. Suitable biological samples include, but are not limited to, human biological matrices, blood, plasma, serum, urine, saliva, synovial fluid, ascitic fluid, or other biological tissue or fluid. For example, the sample may be fresh blood or stored blood or blood fractions. The sample may be a blood sample expressly obtained for the assays of this invention or a blood sample obtained for another purpose which can be subsampled for use in accordance with the methods described herein. For instance, the biological sample may be whole blood. Whole blood may be obtained from the subject using standard clinical procedures. The biological sample may be a blood sample separated out into plasma or serum for analysis. Plasma may be obtained from whole blood samples by centrifugation of anti-coagulated blood.

The biological sample can be measured and analyzed on any devices or combined devices known to one skilled in the art capable of detecting and quantifying amounts of organic molecules, biological metabolites, and/or proteins in the sample, using any method known to one skilled in the art. For example, a mass spectrometer may be used independently or in conjunction with a liquid or gas chromatography instrument or ion mobility spectrometer to analyze the biomarkers in the sample. Alternative instruments used in the sample analysis may include NMR, or devices for immunological detection.

The measurement of levels of the biomarkers in the sample can be carried out with or without sample preparation. The sample may be pretreated as necessary by dilution in an appropriate buffer solution, concentrated if desired, or fractionation or separation of biomarkers from each other by any number of methods including but not limited to ultracentrifugation, chromatography, fractionation by fast performance liquid chromatography (FPLC), or precipitation. Any of a number of standard aqueous buffer solutions, employing one of a variety of buffers, such as phosphate, Tris, or the like, at physiological to alkaline pH can be used.

Measurements of the biomarkers in the sample can be carried out using any suitable devices to measure, among other values, the concentrations, levels of activity, or absolute amounts of the biomarkers. Thus, the terms "quantities," "levels," "amounts," "concentrations," and "levels of activity," when used to describe the amount of biomarkers, are herein interchangeable.

The biomarkers measured relate to at least 3 of the following physiological processes: 1) adipose tissue insulin resistance, 2) pancreatic beta cell dysfunction and/or exhaustion, 3) muscle and/or hepatic insulin resistance, 4) functional enhancement of insulin secretion by beta cells, 5) inhibition of beta cell function, 6) an adipokine, 7) total glycemic control, and 8) inflammation.

For instance, the biomarkers measured may relate to at least the following processes: 1) adipose tissue insulin resistance, 2) pancreatic beta cell dysfunction and/or exhaustion, and 6) an adipokine. In one embodiment, the biomarkers measured relate to the following processes: 1) adipose tissue insulin resistance, 2) pancreatic beta cell dysfunction and/or exhaustion, 3) muscle and/or hepatic insulin resistance, 4) functional enhancement of insulin secretion by beta cells, and 6) an adipokine. In one embodiment, the biomarkers measured relate to the following processes: 1) adipose tissue insulin resistance, 2) pancreatic beta cell dysfunction and/or exhaustion, 3) muscle and/or hepatic insulin resistance, 4) functional enhancement of insulin secretion by beta cells, 5) inhibition of beta cell function, and 6) an adipokine. In one embodiment, the biomarkers measured relate to the following processes: 1) adipose tissue insulin resistance, 4) functional enhancement of insulin secretion by beta cells, 7) total glycemic control, and 8) inflammation. In one embodiment, the biomarkers measured relate to the following processes: 1) adipose tissue insulin resistance, 2) pancreatic beta cell dysfunction and/or exhaustion, 3) muscle and/or hepatic insulin resistance, 6) an adipokine, 7) total glycemic control, and 8) inflammation.

The biomarkers used may relate to adipose tissue insulin resistance. Suitable biomarkers include, but are not limited to, a total free fatty acid or a component fatty acid species of a total free fatty acid.

The biomarkers used may relate to pancreatic beta cell dysfunction and/or exhaustion. Suitable biomarkers include, but are not limited to, c-peptide, intact pro-insulin, and a fragment of any form of insulin.

The biomarkers used may relate to adipokine function. Suitable biomarkers include, but are not limited to, adiponectin, leptin, TNFα, resistin, visfatin, DPP-IV, omentin, and apelin.

The biomarkers used may relate to functional enhancement of insulin secretion by beta cells. Suitable biomarkers include, but are not limited to, L-GPC, an incretin, arginine, and other biological secretagogues and potentiators. The enhancement of beta cell function can be indicated by the presence, absence, or abnormal levels of the biomarkers.

The biomarkers used may relate to inhibition of beta cell function. Suitable biomarkers include, but are not limited to, α-hydroxybutyrate (AHB), glutamate, γ-aminobutyric acid (GABA), and other component with demonstrated beta cell toxicity or suppressor of insulin secretion in response to glucose stimulation.

The biomarkers used may relate to muscle and/or hepatic insulin resistance. Suitable biomarkers include, but are not limited to, ferritin, iron saturation, acyl-carnitine, carnitine, creatine, fibrinogen, and a branched-chain amino acid. As understood by one skilled in the art, the term "iron saturation" refers to a biomarker calculated as the measured amount of iron divided by the measured amount of transferrin in serum.

The biomarkers used may relate to total glycemic control. Suitable biomarkers include, but are not limited to, glucose, HbA1c, fructosamine, glycation gap, D-mannose, and 1,5-anhydroglucitol (1,5-AG), and, optionally, α-hydroxybutyrate (AHB).

The biomarkers used may relate to inflammation. Suitable biomarkers include, but are not limited to, lipoprotein-associated phospholipase A2 (LpPLA2), fibrinogen, high sensitivity C-reactive protein (hsCRP), myeloperoxidase (MPO) and F2-isoprostanes and, optionally, one or more biomarkers selected from the group consisting of serum amyloid A and variants thereof; HSP-70; IL-6; TNF-α; haptoglobin and variants thereof; secretory phospholipase A2 (sPLA2); pregnancy-associated plasma protein-A (PAPP-A); and mannose binding lectin (MBL) level, activity, genetic polymorphisms or known haplotypes thereof.

The biomarkers used in the method may contain at least three from the physiological classes listed above, and at least one from the remaining classes. Alternatively, the biomarkers used in the method may contain at least three from the physiological classes listed above, and at least two from the remaining classes. Alternatively, the biomarkers used in the method may contain at least three from the physiological classes listed above, and at least three from the remaining classes. Alternatively, the biomarkers used in the method may contain at least three from the physiological classes listed above, and at least four from the remaining classes. Alternatively, the biomarkers used in the method may contain at least three from the physiological classes listed above, and at least five from the remaining classes.

The biomarkers used in the method may be from the same or different physiological classes. One or more biomarkers used may relate to more than one physiological process. For instance, glucose may relate to the above processes (1)-(5) and (7); fibrinogen may relate to the above processes (3) and (8). More details about these biomarkers being involving in overlapping physiological processes are shown in Table 1 below.

An exemplary combination of biomarkers measured in the method comprises free fatty acids, c-peptide, and adiponectin. Another exemplary combination of biomarkers measured in the method comprises free fatty acids, c-peptide, adiponectin, ferritin, and L-GPC. Another exemplary combination of biomarkers measured in the method comprises free fatty acids, c-peptide, adiponectin, ferritin, L-GPC, and AHB. Another exemplary combination of biomarkers measured in the method comprises free fatty acids, glucose, myeloperoxidase, and L-GPC. Another exemplary combination of biomarkers measured in the method comprises free fatty acids, glucose, myeloperoxidase, insulin, fibrinogen, and leptin.

The biomarkers used in the method also include those described in Table 1 below. Table 1 lists the panels of predictive and informative diagnostic analytes in 5 different metabolic processes that underpin the development of T2DM.

TABLE 1

Biomarkers in 5 different metabolic processes (note that some analytes may inform more than one category)

| Panel | Core Biomarkers | Optional/Accessory |
|---|---|---|
| Total Glycemic Control | glucose, HbA1c, fructosamine, glycation gap, D-mannose, 1,5 A-G | AHB |
| Beta Cell Function | serum amylase, anti-GAD auto-antibody, c-peptide, intact pro-insulin, c-pep/pro-insulin, AHB | GLP-1, fasting insulin, ratio c-peptide/insulin, ratio intact pro-insulin/insulin, ratio [c-peptide + pro-insulin]/insulin, other autoantibodies against pancreatic islet cells such as amylase alpha2 autoantibody, AHB |
| Insulin Resistance | D-mannose, leptin, adiponectin, ferritin, and Free Fatty Acids (FFA) | Fasting insulin, oleic Acid, L-GPC, GLP-1, alpha hydroxybutyrate, MBL amount, activity, or genetic polymorphisms thereof, BMI, LP-IR Score |
| Inflammation | LpPLA2, fibrinogen, hsCRP, Myeloperoxidase (MPO), F2-isoprostanes | HSP 70, IL-6, TNF-α, SAA variants, haptoglobin variants; secretory phospholipase A2 (sPLA2); pregnancy-associated plasma peptide A (PAPP-A), MBL amount, activity, or genetic polymorphisms thereof. |
| Lipids and Lipoproteins | FFA, triglycerides, RLP, ApoB-48, L-GPC, LP-IR score, LDL-c, HDL-c | Lipid particle measurements; the measurement of cholesterol and/or triglycerides contained within one or more specific subtypes of lipoprotein particles and remnants thereof, and Mannose Binding Lectin, MBL) and associated genetic polymorphisms and known haplotypes thereof |

All protein biomarkers claimed refer to any and all of the variants comprising the "wild type" protein, variants due to SNPs, variants due to differential associations of multiple primary chains into secondary, tertiary, quaternary structures, post-translational modifications, glycosylations, fragments, dimers, trimers, tetramers, and n-mers, etc.

More descriptions about biomarkers and relating physiological processes can be found in PCT/US13/069257, entitled "Method of Determining and Managing Total Cardiodiabetes Risk," filed Nov. 8, 2013; U.S. patent application Ser. No. 14/153,994, entitled "Method of Detection of Early Insulin Resistance and Pancreatic Beta Cell Dysfunction in Normoglycemic Patients," filed Jan. 13, 2014; U.S. patent application Ser. No. 14/216,850, entitled "Method of Generating an Index Score for MBL Deficiency to Predict Cardiovascular Risk," filed Mar. 14, 2014; and U.S. patent application Ser. No. 14/154,074, entitled "Method of Detection of Clinically Significant Post-Prandial Hyperglycemia in Normoglycemic Patients," filed Jan. 13, 2014; all of which are herein incorporated by reference in their entirety.

The biomarker measured in the method can be a protein in a form of a monomer, a multimer, a complex with one or more other organic molecules, a normal (wild-type) form, a genetic variant with altered amino acid sequence or conformation, an isoform, a glycoform, a post-translationally modified form, an oxidized form, a form with altered biological function, a fragment/product of enzymatic cleavage, or an adduct with another chemical moiety.

After obtaining measured levels of a combination of the biomarkers, the measured values are mathematically transformed by means of an algorithm to generate a score.

The mathematical transformation can comprise the steps of: i) multiplying the measured level of each of the biomarkers by a pre-determined exponent; ii) multiplying the products of the exponentiation generated from step i); and iii) logarithmically transforming the multiplied product generated from step ii).

As will be understood by one skilled in the art based on the teachings herein, the algorithm and the exponent for each biomarker in the algorithm can be determined by a variety of techniques and can vary widely. In one example of determining appropriate exponent for each biomarker, multivariable logistic regression (MLR) is performed using the biomarker values found in the patients to predict the IGT determined by a 2-hour OGTT. The pre-determined exponent for each biomarker can be derived from values within the 90% confidence interval of the biomarker measurement distribution in a population study. For instance, the predetermined exponent for each biomarker is the median or mean from values within the 90% confidence interval of the biomarker measurement distribution in the population study. There are several methods for variable (biomarker) selection that can be used with MLR, whereby the biomarkers not selected are eliminated from the model and the exponents for each predictive biomarker remaining in the model are determined. These exponents are then multiplied by the biomarker content of the sample (expressed as a percentage of total biomarkers in the sample) and then summed to calculate a weighted score. The resulting score can then be compared with a particular cutoff score (i.e., a threshold), above which a subject is diagnosed having high likelihood of having abnormal glucose tolerance (or increased likelihood of early insulin resistance). A statistical model that may be used to derive the algorithm and the exponent for each biomarker in the algorithm is exemplified in Example 1.

An exemplary algorithm comprises obtaining the amounts of the biomarker analytes from at least three of the physiological classes listed in step (a) above, and optionally at least one, two, three, four, or five of the remaining classes; multiplying the amount of each analyte component (biomarker) by an exponent; then multiplying each respective values of measured analyte component after the exponentiation; and taking the natural log of the multiplied product.

The exponents of the respective measured component values included in the algorithm can be derived from a population study. For example, the exponents for individual components can be chosen from the range of actual measured values within the 90% confidence interval of the distribution of values for each respective component in the population study, with particular preference for selection of the median or mean values within the 90% confidence internal of a distribution of the measurements of respective components in the population study.

Scores can be calculated based on the following exemplary algorithms, as described in Examples 2-6:

$$Ln\left[\frac{FFA^{0.825} * Cpeptide^{0.729}}{Adiponectin^{0.137}}\right];$$

$$Ln\left[\frac{FFA^{0.807} * Cpeptide^{0.688} * Ferritin^{0.0447}}{LGPC^{0.0852} * Adiponectin^{0.130}}\right];$$

$$Ln\left[\frac{FFA^{0.774} * Cpeptide^{0.679} * AHB^{0.0655} * Ferritin^{0.0407}}{LGPC^{0.0848} * Adiponectin^{0.131}}\right];$$

$$Ln\left[\frac{FFA^{1.838} * Glucose^{6.386} * MPO^{2.001}}{LGPC^{1.432}}\right]; \text{ and}$$

$$Ln\left[\frac{FFA^{2.374} * Glucose^{5.248} * MPO^{1.741} * Insulin^{1.037} * Fibrinogen^{3.037}}{Leptin^{0.601}}\right].$$

As used herein, a "control" or "reference value" is an empirical value (score) derived from a normal human subject or from a population study using the algorithms herein, depending on the biomarkers used in the algorithms. The likelihood of a subject having abnormal glucose tolerance or early insulin resistance is relative to the control score or reference value. In one embodiment, the reference value is derived from pre-defined, empirical calculation of OGTT scores based on the biomarker levels from a normal individual or population (i.e., known to have normal glucose tolerance, e.g., a 2-hour OGTT test. In one embodiment, the reference value is derived from pre-defined, empirical calculation of OGTT scores based on the biomarker levels from a population of randomly chosen subjects, with or without normal glucose tolerance. In one embodiment, when the empirical scores from a population study is used, the normal distribution of which can be used to determine the control or reference value, e.g., the score from the bottom 5%, 10%, 15%, 20%, 25%, or 50% of the population can be used as a cutoff value, i.e., a reference value. A score higher than this reference value correlates with an increased likelihood of the subject having abnormal glucose tolerance, and a score lower than this reference value correlates with a decreased likelihood of the subject having abnormal glucose tolerance.

The resulting score is correlated to the likelihood (odds ratio) of elevation of blood glucose to ≥140 mg/dL at 2 hours post oral glucose tolerance test (OGTT) and/or a mixed meal challenge.

The score generated by the algorithm is an odds ratio that corresponds to the likelihood that a patient will have a true positive IGT. The odds ratio is a measure of relative risk determined by logistic regression. When compared to a reference value from a population study, an elevated score correlates with an increased likelihood of elevation of blood glucose to ≥140 mg/dL at 2 hours after oral glucose tolerance test and indicates that the subject has an increased likelihood of having abnormal glucose tolerance; and a low score correlates with a decreased likelihood of elevation of blood glucose to ≥140 mg/dL at 2 hours post oral glucose tolerance test and indicates that the subject has a decreased likelihood of having abnormal glucose tolerance.

For example, Table 5 shows the odds ratios for the 3 illustrative examples of the algorithms derived in Examples 2-4. The interpretation is that for every increase of the algorithm score of 1 SD, the odds of a subject having IGT increase by a given amount. For instance, in column 2 of Table 5, the odds ratio for version 1 of the algorithm (Example 2) is 3.57, indicating that on a continuous scale, each increase in the algorithm score by 1 SD above the mean results in a patient being 3.57 times more likely to have IGT.

The area under receiver operating characteristic (ROC) curves (AUC, c-statistics, concordance index) can summarize the continuum of model sensitivity and specificity values into a single measure. Positive likelihood ratios combine in one number the sensitivity and specificity at the cut-point threshold by dividing the proportion of true positives by the proportion of false positives. This statistic indicates how likely it is that a case will have an abnormal test compared to a reference, given 2 random patients, one of whom is a case and the other a reference. The c-statistics (AUC) shows the accuracy and sensitivity of the prediction from a method. Typically, the method predicts the likelihood (odds ratio) of elevation of blood glucose to ≥140 mg/dL at 2 hours post OGTT with a c-statistic (AUC value in an ROC plot) of at least 0.70.

The resulting score generated by the method may be used as a proxy for a 2-hour time point blood glucose measurement, and can replace the oral glucose tolerance test (OGTT) to predict likelihood of the subject having abnormal glucose tolerance.

The method can further comprise obtaining values for one or more base model factors to predict the likelihood of the subject having abnormal glucose tolerance; calculating a based model score for the subject based on one or more values of the base model factors; and combining the score obtained from step b) (i.e., the score calculated based on the measured levels of the biomarkers via a mathematical transformation) with the calculated base model score. The combined score can then be compared to reference values from a population. Exemplary base model factors are age, sex, BMI, fasting glucose, HbA1C, and fasting insulin.

Figure 3:
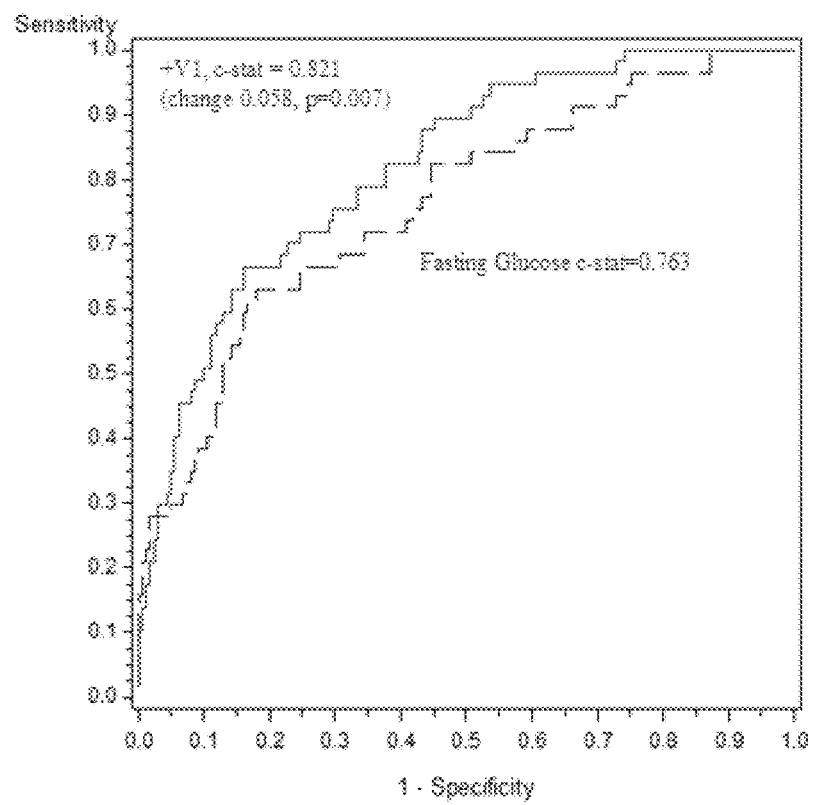
FIG. 3 is a graph showing the change in area under the ROC curve tested when Version 1 of the OGTT Fasting Index was added to the base model that included age, sex, BMI, and fasting glucose.
Figure 4:
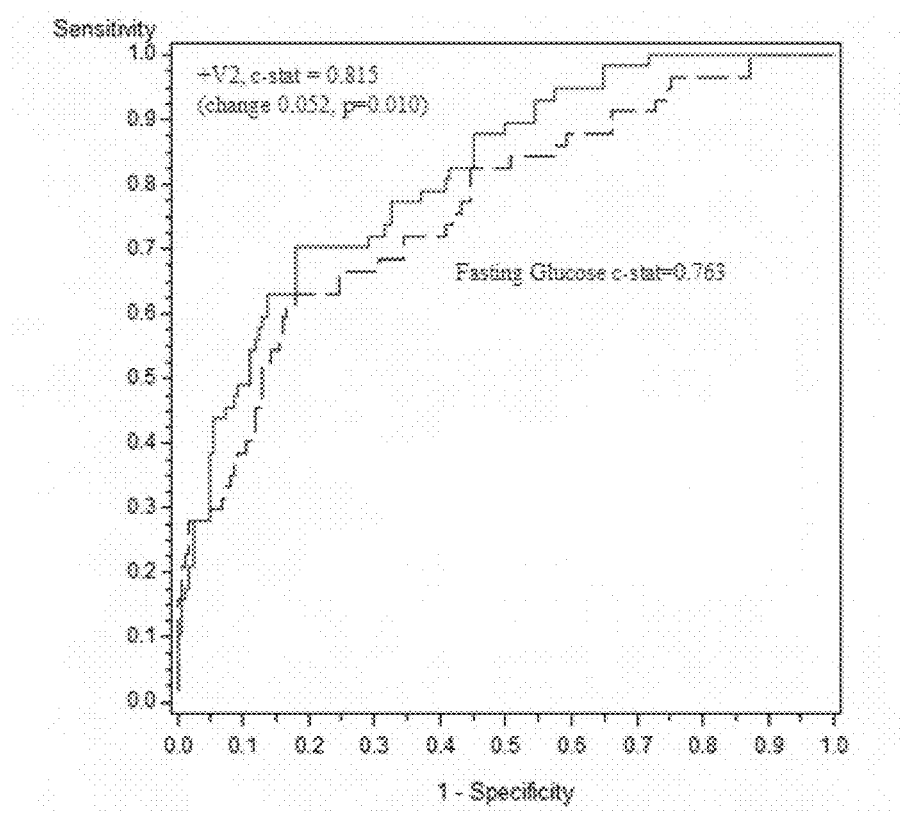
FIG. 4 is a graph showing the change in area under the ROC curve tested when Version 2 of the OGTT Fasting Index was added to the base model that included age, sex, BMI, and fasting glucose.
Figure 5:
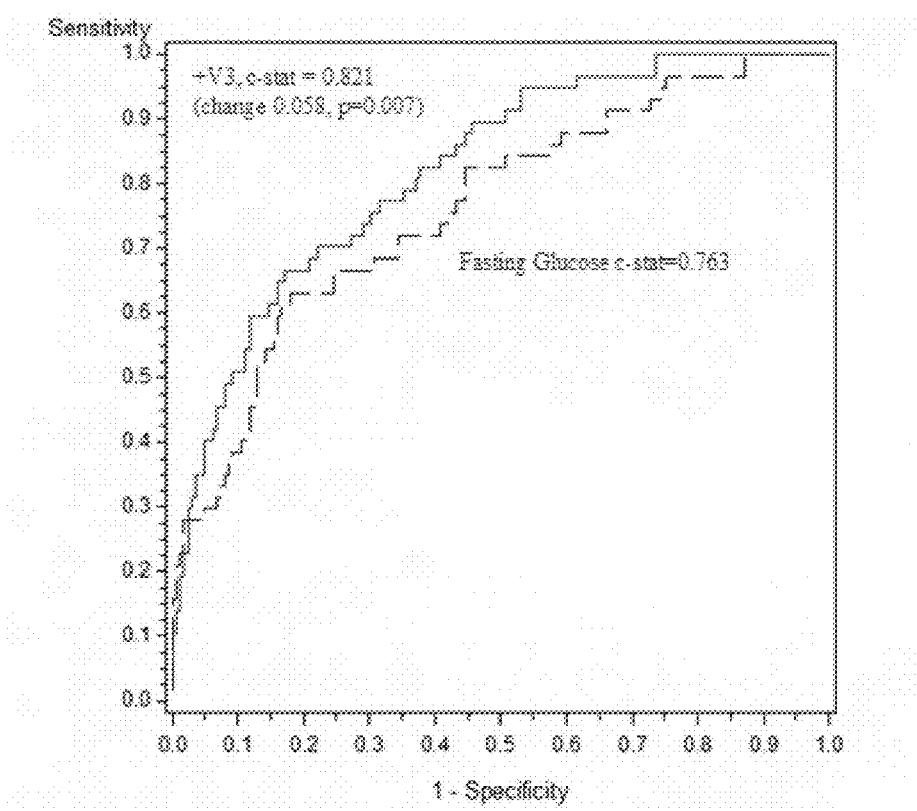
FIG. 5 is a graph showing the change in area under the ROC curve tested when Version 3 of the OGTT Fasting Index was added to the base model that included age, sex, BMI, and fasting glucose.
Figure 6:
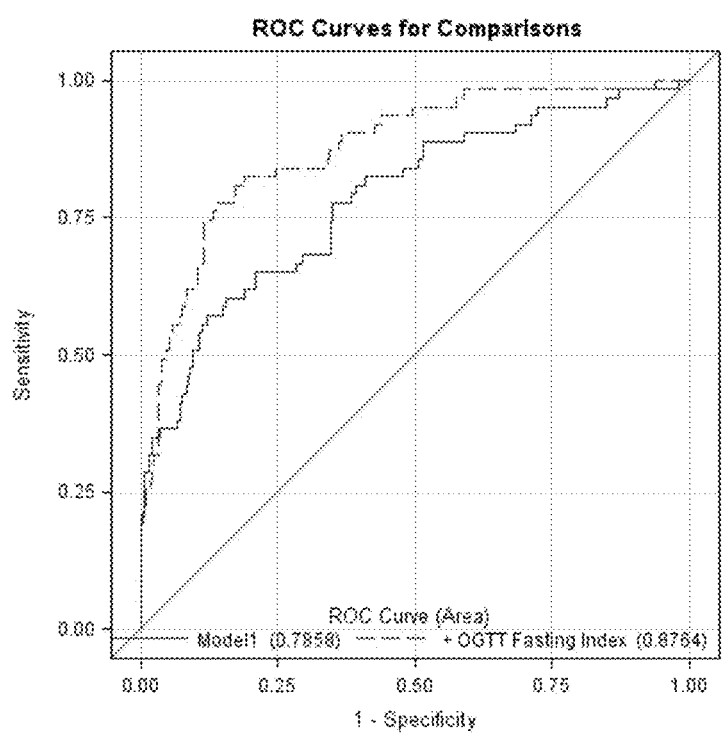
FIG. 6 is a graph showing the change in area under the ROC curve tested when Version 4 of the OGTT Fasting Index was added to the base model that included age, sex, BMI, fasting glucose, HbA1C, and fasting insulin.
Figure 7:
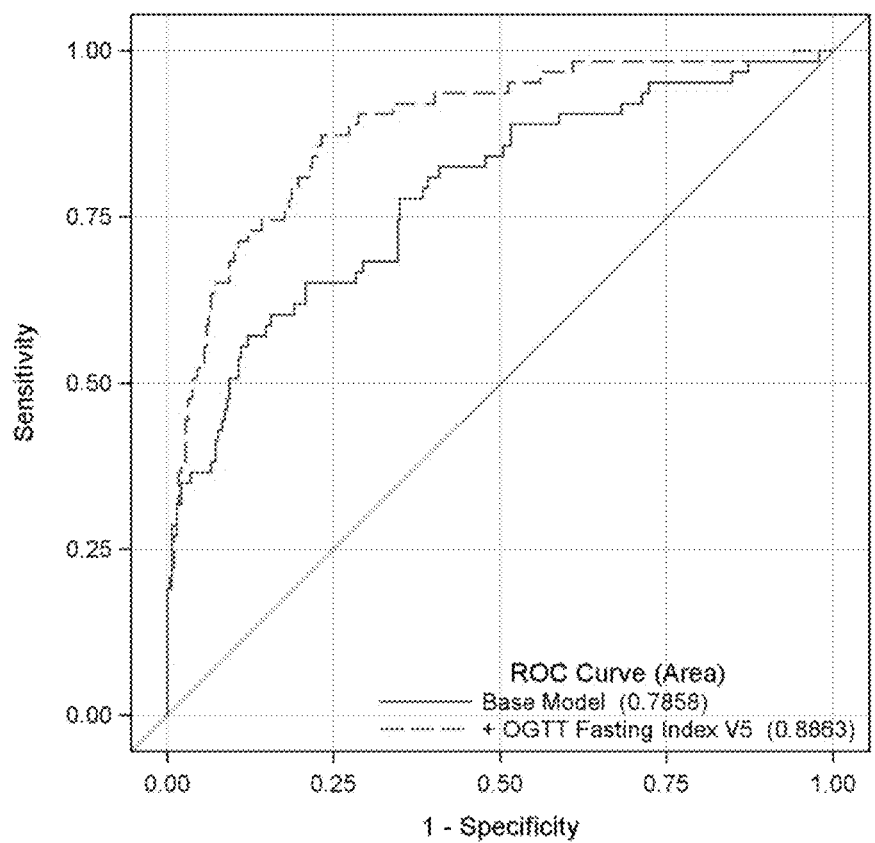
FIG. 7 is a graph showing the change in area under the ROC curve tested when Version 5 of the OGTT Fasting Index was added to the base model that included age, sex, BMI, fasting glucose, HbA1C, and fasting insulin.

For instance, as shown in Table 5, the base model factors can include age, sex, BMI, and fasting glucose. In one embodiment, the base model factor is fasting glucose. In this case, the base model score is calculated by logarithmically transforming a measured level of fasting glucose in the subject. FIGS. 3-5 illustrate the change in area under the curve (AUC) in an ROC plot when the algorithmic score for the 3 models described in Examples 2-4 are added to the base model. The base model contains the variables age, sex, BMI, and fasting glucose, the most predictive of which is fasting glucose. As shown in Table 5 and FIGS. 3-5, combining the score obtained from step b) of the method with the base model score provides an improved likelihood prediction than the base model score alone: the c-statistics (AUC) for the scores combining each equation with the base model were significantly greater than the base model alone. Surprisingly, the algorithm alone provides an improved likelihood prediction than the base model. As shown in Table 5, the c-statistics (AUC) for the scores from each equation alone were greater than the base model.

The score calculated from the algorithm can also be used to reclassify a patient from NGT to IGT, and vice versa. The term "reclassification" refers to the continuous net reclassification improvement (NRI) achieved by the addition of the algorithm score to the base model (e.g., fasting glucose) as a predictor of likelihood of IGT, as defined by elevated 2-hour glucose over 140 mg/dL. The term "reclassification" includes both reclassification of patients from NGT in the base model to IGT in the model including the algorithmic score, and patients from IGT in the base model to NGT in the model including the algorithmic score. For instance, in Table 5, combining the score obtained from step b) with the base model score causes a net reclassification improvement (NRI) of the subject from having normal glucose tolerance (NGT) to impaired glucose tolerance (IGT), or from having IGT to NGT. NRI can be continuous NRI or clinical NRI. Clinical NRI is based on reclassifying subjects around already established risk categories. Typically, continuous NRI is reported, which is the sum of the percentages of the cases reclassified plus the percentages of the controls reclassified. It is reported as a net reclassification improvement, which means that some cases and controls may be classified in the wrong direction, but overall, there is an improvement with a positive number. Typically, a test that reclassifies a net 10% of subjects would be useful. The net reclassification improvement can be at least 10%, at least 20%, at least 30%, at least 40%, or at least 50%. In one embodiment, the net reclassification improvement is at least 56%.

Inherent in this description of the continuous net reclassification improvement and odds ratios discussed in [0050] and Table 5 is the concept that the risk of being a true positive IGT rises with increasing algorithm score, and thus, patients may be designated as low, intermediate, or high risk of being a true positive IGT based on their algorithm score. Score cutoffs can be set, for example, at the boundaries of the tertiles, quartiles, quintiles, etc., of score distribution, grouping patients with similar relative risks. The relative risk for each group could be averaged over the group and presented as an odds ratio relative to the lowest risk group, for example. Alternatively, the relative risk could be expressed by stating that a given value places the patient at X % risk higher relative to the entire population (the normal distribution) determined by an empirical study. It will be appreciated that empirical clinical studies employing the data analysis and statistical methods described herein may yield odds ratios or optimal cutoffs that vary slightly between populations, i.e. racial differences, geographical differences, etc. The algorithms or the risk cutoffs can be adjusted accordingly and still be within the bounds of the invention, provided that the alterations are supported by an empirical study.

The method may be used once, or repeatedly, for prediction of likelihood of an abnormally high 2-hour glucose at or above 140 mg/dL.

The method may be used to predict the likelihood of a subject having abnormal glucose tolerance by a single measurement of a single fasting sample.

Alternatively, the method may further comprise monitoring the levels of the biomarkers in the subject to assess progression, improvement, normalization, and/or treatment efficacy. The monitoring step comprises repeating steps a)-c) of the method based on the levels of the biomarkers from a biological sample in the subject obtained at a later time.

The resulting score of the method may be used to define a cardiodiabetic risk level, and/or for monitoring disease progression and/or for monitoring response to treatment. Thus, the resulting score can further correlate with the risk of cardio-diabetic condition and comorbidities, in which an elevated score correlates with an increased risk of cardio-diabetic condition and comorbidities, and a low score correlates with a decreased level of risk of cardio-diabetic condition and comorbidities. Moreover, a numerical or categorical classification of risk can be assigned based on the resulting score.

The resulting score of the method may be used to further correlate to the likelihood that a patient is experiencing elevation of blood glucose to ≥140 mg/dL at 2 hours in an uncontrolled non-clinical setting where the amount and composition of meals varies.

The method can be used to predict the likelihood of a subject having abnormal glucose tolerance at various situations. For example, the glucose tolerance of the subject may be unknown at the time the method is carried out. Alternatively, the glucose tolerance of the subject can be presumed to be normal at the time the method is carried out. Alternatively, the glucose tolerance of the subject can be presumed to be impaired at the time the method is carried out.

The method can be used to predict likelihood of a subject having abnormal glucose tolerance regardless whether the subject is or is not receiving or has or has not previously received a therapy for a diabetic condition.

The resulting score can be used to assess a subject's health and/or need for a therapy regimen. The resulting score can be used by a healthcare practitioner to prescribe a therapy regimen.

The resulting score in repeated measurements can be used to assess progression, improvement, normalization, and/or treatment efficacy.

The resulting score in repeated measurements can also be used to assess the need to change therapy regimen. Under this condition, the change in the repeat measurements can be compared to the baseline measurements, and the comparison can result in reclassification of numerical or categorical risk level of cardiodiabetic condition and comorbidities.

Thus, the method may further comprise administering a therapy regimen to a subject for the treatment or prevention of abnormal glucose tolerance.

Another aspect of the invention relates to a method of accessing insulin sensitivity in a subject. The method comprises the step of obtaining, from a biological sample in a subject, measured levels of a combination of biomarkers relating to at least three of the following physiological processes: adipose tissue insulin resistance, pancreatic beta cell dysfunction and/or exhaustion, muscle and/or hepatic insulin resistance, functional enhancement of insulin secretion by beta cells, inhibition of beta cell function, and adipokine function isolated from a subject. The method further comprises comparing the measured levels of the biomarkers to glucose disposal reference levels of the biomarkers. A glucose disposal rate lower than the glucose disposal reference levels indicates an increased likelihood of early insulin resistance, and a glucose disposal rate higher than the glucose disposal reference levels indicates a decreased likelihood of early insulin resistance.

The detailed steps for obtaining biological samples, identifying the biomarkers, measuring levels of the biomarkers, comparing the measured levels of the biomarkers to the reference levels, and comparing the result to predict insulin resistance are similar to the detailed steps described in the above embodiments for method of predicting likelihood of a subject having abnormal glucose tolerance.

Diabetes and Related Disease Conditions

Diabetes, or diabetes mellitus (DM), is a group of diseases characterized by high blood glucose levels that result from defects in the body's ability to produce and/or use insulin. Diabetes encompasses Type 1 diabetes and Type 2 diabetes, which are chronic conditions, and gestational diabetes, which occurs during pregnancy and may resolve itself after the baby is delivered. A precursor to Type 2 diabetes is the potentially reversible-condition prediabetes, which refers to a condition when blood sugar levels are higher than normal but not high enough to be considered diabetes. Prediabetes and Type 2 diabetes result from the body's inability to use insulin efficiently, a condition known as insulin resistance. If left untreated, insulin resistance leads to full-blown Type 2 diabetes.

The control of blood glucose levels is critical to human health. Insulin plays a central role in glucose regulation: it is the hormone that brings blood glucose into cells. Without sufficient insulin to bring glucose into the cells, blood glucose becomes elevated, the cells "starve" for glucose, and the body must use alternative pathways to produce energy for vital organs, e.g., generating ketone bodies and free fatty acids (FFAs) to fuel the brain and heart, respectively. The pancreatic beta cells normally secrete insulin in response to a meal or a "glucose load" during an oral glucose tolerance test (OGTT), thus lowering the level of blood glucose by bringing glucose into the cells of the body. This process of glucose homeostasis can be dysregulated in a number of ways, resulting in poor control of blood glucose levels. When a patient's glucose balance is dysregulated such that the patient's blood glucose level becomes higher than normal for short or long periods of time, it indicates that the patient has developed or is developing diabetes.

Type 1 diabetes (T1DM) is a type of diabetes formerly known as "early onset" diabetes because it is an acute illness usually occurring in childhood or adolescence, but becomes evident in adults. In this condition, the patient will suddenly become very sick, with high blood sugar due to rapid and catastrophic failure of the pancreas to produce enough insulin. The patient requires injections of insulin in order to maintain normal levels of blood sugar to survive. The cause is commonly understood to derive from a viral infection and/or autoimmunity. Full-blown T1DM requires that patients be treated with exogenous insulin, because patients do not make enough insulin by themselves to survive. However, there are milder forms of T1DM that progress more slowly to insulin-dependence, or in which a patient may need insulin for a short period of time, and then go off of insulin and maintain their normal blood glucose regulation.

Type 2 diabetes (T2DM) is different physiologically than T1DM. T2DM is characterized by abnormally high blood glucose and abnormally high insulin levels. Also, T2DM does not have an acute onset of symptoms like T1DM. In contrast, it develops gradually over time, usually years, and therefore was formerly known as "adult onset" diabetes. T2DM is related to diet and lifestyle factors such as eating a high-sugar, high-carb diet, lack of exercise, and development of obesity, in particular abdominal obesity. Because of the sedentary lifestyle and poor diet in the western world, there is an epidemic of T2DM in the US and Europe that parallels the rise in the number of obese and morbidly obese adults. Because more children are also becoming obese, more cases of T2DM are developing in childhood. The consequences for development of T2DM is a radical increase in the risk of cardiovascular disease, termed cardio-diabetes, such as increased risk of heart attacks, strokes, high blood pressure, atherosclerosis, coronary artery disease, and related conditions.

Insulin resistance (IR) is the earliest stage of T2DM. The development of T2DM is preceded by a substantial period of abnormal metabolism during which lifestyle and diet intervention, including weight loss, can completely prevent and reverse the development of the disease in most people. Most patients exhibit signs of metabolic syndrome, as described below. Patients with insulin resistance generally have conditions such as hyperinsulinemia, impaired glucose tolerance, dyslipidemia (hypertriglyceridemia and decreased high-density lipoprotein (HDL) cholesterol) and hypertension. Chronic inflammation may also drive the development of insulin resistance. Insulin resistance is a change in physiologic regulation such that a fixed dose of insulin causes less of an effect on glucose metabolism than it typically causes in normal individuals, i.e., blood glucose in insulin-resistance patient does not drop as much or as fast as it should in response to increases in insulin. The normal compensatory response to insulin resistance is an even higher increase in insulin secretion that results in hyperinsulinemia. If the hyperinsulinemia is sufficient to overcome the insulin resistance, glucose regulation remains normal; if not, type 2 diabetes ensues.

"Metabolic syndrome" is associated with insulin resistance. It is a cluster of metabolic abnormalities involving body fat distribution, lipid metabolism, thrombosis, blood pressure regulation, and endothelial cell function. This cluster of abnormalities is referred to as the insulin resistance syndrome or the metabolic syndrome. Eventually, blood glucose remains elevated even in the fasting state as the insulin-resistant patient progresses towards T2DM. The pancreatic beta cells wear out pumping the required insulin, and over time, the pancreatic islets (and the beta cells they contain) are damaged perhaps due to the exhaustion. The pancreatic beta cells begin to secrete more immature insulin (pro-insulin) in an attempt to keep up with the demand, and therefore, in the blood of insulin-resistant patient who is developing T2DM, biomarkers of pancreatic beta cell dysfunction such as higher levels of insulin, pro-insulin and c-peptide (Singh et al., "Surrogate markers of insulin resistance: A review," World J Diabetes 1(2): 36-47 2010, which is hereby incorporated by reference in its entirety) can present.

The term "pre-diabetes" is essentially synonymous with insulin resistance and metabolic syndrome of Type 2 diabetes, but has specific laboratory-measured values associated with it. Doctors screen patients for diabetes if they have known risk factors, a family history of diabetes, high blood pressure, BMI greater than 25, or if they have abnormal cholesterol levels (defined as HDL-C below 35 mg/dL (0.9 mmol/L) or triglyceride level above 250 mg/dL (2.83 mmol/L).

If full-blown T2DM develops and is left undiagnosed and untreated, patients should be treated with insulin-sensitizing drugs which may help make their cells more responsive to insulin so that the pancreas does not have to work as hard. Blood glucose balance can be maintained with insulin sensitizing drugs, or maintained and/or reversed by effectuating diet and lifestyle modifications and weight loss. Unlike full-blown T1DM, T2DM may be reversible in many patients. However, if T2DM progresses far enough, the pancreatic beta cells become unable to secrete enough insulin on their own due to exhaustion, and the patients may progress to the last stage of T2DM where they cannot make enough insulin. Thus, the patients will become insulin-dependent and need exogenous insulin injection to survive, because their pancreatic beta cells no longer function. This is the worst stage of T2DM and can be fatal because while a patient can be administered exogenous insulin, their body may still be resistant to its effects. These patients are at dramatically increased risk for cardio-diabetic morbidity and mortality.

Diagnoses of Abnormal Glucose Metabolism

Disorders of glucose metabolism on the sliding scale of T2DM are defined per the following laboratory test values:

Diabetes (or diabetes mellitus) is diagnosed clinically by demonstrating any of the following four criteria (results should be confirmed by retesting on a subsequent occasion): fasting glucose level ≥126 mg/dL; glycosylated hemoglobin (HbA1C) level ≥6.5%; 2-hour glucose level ≥200 mg/dL during glucose tolerance testing (e.g., two hours after a 75 g oral glucose load); random glucose values ≥200 mg/dL in the presence of symptoms of hyperglycemia.

Insulin resistance (IR) is diagnosed clinically according to the following laboratory analysis: a state in which higher concentrations of insulin are required to exert normal effects; blood glucose levels may be normal but fasting insulin levels may be high because of compensatory insulin secretion by the pancreas. Insulin levels can be defined for certain individuals. For instance, in some tests at Health Diagnostic Laboratory, Inc., optimal fasting insulin level is defined as 3-9 µU/mL, intermediate insulin level is defined as >9 µU/mL and <12 µU/mL, and high insulin level is defined as ≥12 µU/mL.

"Pre-diabetes" can be diagnosed by demonstrating one of the following: the glycated hemoglobin (HbA1C) level of 6.0% to 6.5%, a fasting blood glucose level from 100 to 125 mg/dL (or 5.6 to 6.9 mmol/L), or a blood glucose value of 140 to 199 mg/dL (or 7.8 to 11.0 mmol/L) at the 2-hour time point of an OGTT. If the patient has pre-diabetes, doctors will usually check fasting blood glucose, HbA1C, total cholesterol, HDL cholesterol, low-density lipoprotein (LDL) cholesterol, and triglycerides at least once a year.

"Impaired glucose tolerance (IGT)" is assessed by typically evaluating if glucose levels are 140-199 mg/dL 2 hours after a 75 g oral glucose load. The elevation of 2-hour blood glucose value indicates a patient has an IGT.

Impaired fasting glucose is diagnosed by typically evaluating if fasting glucose levels (i.e., glucose levels after an 8-hour fasting) are 100-125 mg/dL 2 hours after a 75 g oral glucose load. The elevation of 2-hour blood glucose value indicates a patient has an IGT.

It will be appreciated by those skilled in the art of diabetes diagnostics and treatment that the patient population in which this invention has clinical utility do not fit the above clinical definitions for insulin resistance, pre-diabetes, metabolic syndrome, impaired fasting glucose, T2DM, or T1DM (insulin-dependent). This test does not detect insulin resistance or place a patient on a scale between normal glucose tolerance (NGT) and diabetes, because the patient population in which the test predicts abnormal first-phase insulin response are by definition NGT with normal glucose and insulin levels at baseline and the 2 hour time point, and do not meet the definition of insulin resistance based on their lipid values on the LP-IR scale. Thus, while for the purpose of illustrating the utility of the invention we split the patients into groups by glucose tolerance and degree of insulin resistance for the purpose of analyzing data in the different groups, this is for illustrative purposes to show the utility of the test in the NGT, non-insulin resistant "normal" group. The test does not have clinical utility as an early predictor of risk once the patient has met the criteria for Impaired Glucose Tolerance (IGT) or Diabetes.

Therapy Regimen

After the subject is determined to have an increased likelihood of having abnormal glucose tolerance or early insulin resistance, a therapy/treatment regimen can be selected based on the elevated score to prevent the subject from developing or treat the subject for diabetes or related cardio-diabetes condition and comorbidities.

Methods according to the invention may also involve administering the selected therapy regimen to the subject. Accordingly, the invention also relates to methods of treating a subject to reduce the risk of diabetes or related cardio-diabetes condition and comorbidities.

The selected therapy regimen can comprise administering drugs or supplements. The drug or supplement may be any suitable drug or supplement useful for the treatment or prevention of diabetes and related cardio-diabetes condition and comorbidities. Examples of suitable agents include an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a PCSK9 inhibitor, an MTP inhibitor, mipmercin, a calcium channel blocker, a beta-adrenergic receptor blocker, an angiotensin system inhibitor, a glitazone, a GLP-1 analog, thiazolidinedionones, biguanides, neglitinides, alpha glucosidase inhibitors, an insulin, a dipeptidyl peptidase IV inhibitor, metformin, a sulfonurea, peptidyl diabetic drugs such as pramlintide and exenatide, or combinations thereof. The agent is administered in an amount effective to treat diabetes or related cardio-diabetes condition and comorbidities, or to lower the risk of the subject developing a future diabetes or related cardio-diabetes condition and comorbidities.

The drugs and/or supplements (i.e., therapeutic agents) can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, intranasal drops). Typically, oral administration is the preferred mode of administration.

A therapy regimen may include providing a report to a qualified healthcare provider and/or patient, or providing a referral to a healthcare specialist or related specialist based on the determined score. The reports may be related to the subject's likelihood of developing diabetes or related cardio-diabetes condition and comorbidities based on the determined score. The reports may include suggested therapy regimens selected based on the subject's diabetes or related cardio-diabetes condition and comorbidities.

The report may take the form of a written report, a verbal discussion, a faxed report, or an electronic report accessed by a computing device or hand-held smart-phone device. Comments may be added to the report that aid in data interpretation, diagnosis, and choice of therapy. This report may be transmitted or distributed to a qualified healthcare provider or directly to the patient. Following transmission or distribution of the report, the subject may be coached or counseled based on the therapy recommendations.

Qualified healthcare provider is defined as a physician (MD, DO), nurse, registered dietician, pharmacist, health consultant, or other appropriately trained individual qualified to counsel patients on health-related issues. Healthcare specialists may be a cardiologist, endocrinologist, opthamologist, lipidologist, weight loss specialist, registered dietician, "health coach", personal trainer, etc. Further therapeutic intervention by healthcare specialists based on the determined score may take the form of cardiac catherization, stents, imaging, coronary bypass surgeries, EKG, Doppler, hormone testing and adjustments, etc.

A therapy regimen may also include giving recommendations on making or maintaining lifestyle choices useful for the treatment or prevention of diabetes or related cardio-diabetes condition and comorbidities based on the results of the score. The lifestyle choices can involve changes in diet, changes in exercise, reducing or eliminating smoking, or a combination thereof. For example, the therapy regimen may include glucose control, lipid metabolism control, weight loss control, and smoking cessation. The lifestyle choice is one that will affect risk for developing or having diabetes or related cardio-diabetes condition and comorbidities.

The recommendations may be provided by a healthcare provider. The healthcare provider can repeat an interaction with a patient after a period of time to reinforce recommendations and monitor progress.

Monitoring can also assess the risk for developing further diabetes or related cardio-diabetes condition and comorbidities. This method involves determining if the subject is at an elevated risk for developing diabetes or related cardio-diabetes condition and comorbidities, which may include assigning the subject to a risk category selected from the group consisting of high risk, intermediate risk, and low risk (i.e., optimal) groups for developing or having diabetes or related cardio-diabetes condition and comorbidities. This method also involves repeating the determining if the subject is at an elevated risk for developing diabetes or related cardio-diabetes condition and comorbidities after a period of time (e.g., before and after therapy). The method may also involve comparing the first and second risk categories obtained at different period of time, and determining, based on the comparison, if the subject's risk for developing diabetes or related cardio-diabetes condition and comorbidities has increased or decreased, thereby monitoring the risk for developing diabetes or related cardio-diabetes condition and comorbidities.

System for Predicting Likelihood of Abnormal Glucose Tolerance or Insulin Resistance The methods described herein may be implemented using any device capable of implementing the methods. Examples of devices that may be used include, but are not limited to, electronic computational devices, including computers of all types. When the methods are implemented on a computer, the computer program that may be used to configure the computer to carry out the steps of the methods may be contained in any computer readable medium capable of containing the computer program.

For example, the computer system can optionally comprise a module configured to obtain measured level of a combination of biomarkers from a biological sample in a subject. The computer system can optionally comprise a measuring module configured to yield detectable signal from an assay indicating the amount of each biomarker in the sample. The computer system can further optionally comprise a calculating module configured to calculate a score based on the measured levels of the biomarkers using a mathematical transformation. Optionally, the computer system can comprise a storage module configured to store output information from the calculating module. Optionally, the computer system can comprise an output module for displaying the output information from the calculating module, or generating a report from the output information for the user.

The measuring module may comprise an assay that is automated on robotic equipment.

The calculating module may comprise a software to automate the calculation of the score. The calculating module may also comprise a software to calculate predetermined parameters (e.g., exponents of the biomarkers used in the algorithm).

The computer program, including the reference levels of the biomarkers and base model factors, and predetermined parameters (e.g., exponents of the biomarkers used in the algorithm) may be contained in a computer readable medium. Examples of computer readable medium that may be used include but are not limited to diskettes, CD-ROMs, DVDs, ROM, RAM, and other memory and computer storage devices.

The computer system that may be used to configure the computer to carry out the steps of the methods may also be provided over an electronic network, for example, over the internet, world wide web, an intranet, or other network. It can also be downloaded to a computer or other electronic device such as a laptop, smart-phone, tablet, or the IT network in a provider's office. An exemplary application that carries out the steps of the methods downloadable to a computer or a smart-phone has been described in details in U.S. patent application Ser. No. 14/144,269, entitle "An Interactive Web-based Platform for Facilitating Biomarker Education and Patient Treatment Analysis," filed Dec. 30, 2013; which is herein incorporated by reference in its entirety.

EXAMPLES

The following examples are for illustrative purposes only and are not intended to limit, in any way, the scope of the present invention.

Example 1

Clinical Study and Statistical Models

Clinical Study

The clinical study included 219 subjects who had not been diagnosed with diabetes, but with one or more of the following clinical indications: obesity, history of first-degree family members with diabetes, and presence of one or more components of the metabolic syndrome including impaired fasting glucose.

The subjects underwent a 75 g oral glucose tolerance test (OGTT) and fasting blood collection to evaluate risk of diabetes between March 2012 and May 2013 at several outpatient centers across the US (Madison, Wis.; Jackson, Miss.; Montgomery, Ala.; Charleston, S.C.; Seattle, Wash.; and Salt Lake City, Utah). The clinical indications for testing Patients who tested positive for Anti-GAD autoantibody (titer >5 IU/ml) were excluded from this study regardless of T1DM or LADA status. The study protocol was approved by Copernicus Group IRB (NC).

Samples were sent by overnight courier to Health Diagnostic Laboratory, Inc. ("HDL," Richmond, Va.) for measurement of glucose, insulin, metabolites, and other biomarkers. All laboratory measurements were performed at HDL. Fasting blood samples were collected before the administration of glucola (a sweetened solution containing 75 mg glucose), which was consumed within 5 minutes. Additional blood samples were collected at time intervals of either (1) 30, 60, 90, and 120 minutes, or (2) 60 and 120 minutes, from completion of the administration of glucola. All patients avoided eating, drinking, or smoking during the testing period. Glucose tolerance testing was performed according to a standardized protocol. Insulin resistance (IR) was defined by one or more of the following conditions: fasting glucose ≥100 mg/dL, 2-hour glucose ≥140 mg/dL, HbA1c ≥5.7%, and fasting insulin ≥12 µU/mL. Transient hyperglycemia (TH) was defined as 30, 60, or 90-minute glucose ≥140 mg/dL during OGTT.

Data obtained from the 219 participants were analyzed while additional study subjects were being qualified and enrolled and additional samples were being accrued. Examples 2, 3, and 4 represent the results derived from the analyses of samples collected from the first 219 study subjects.

An additional 133 subjects were included in the final cohort study, for a total of 352 subjects. The selection criteria, testing methods, and sample analyses for the additional 133 subjects are the same as those for the first 219 subjects. Examples 5 and 6 represent the results derived from the analyses of samples collected from all 352 subjects.

Statistical Model

The oral glucose tolerance test (OGTT) fasting index (score) was developed using multiple linear regression to predict C-peptide AUC * FFA AUC during a 2-hour OGTT. Each version of the equations below in Examples 2-6 uses a different combination of biomarkers to develop the OGTT fasting index (score) to predict C-peptide AUC * FFA AUC during a 2-hour OGTT.

Several variable selection methods were used (e.g. stepwise and backwards with Akaike Information Criterion and Schwartz Bayesian Criterion) on a set of blood biomarkers to determine a consistent set of predictor variables (the exponent of each biomarker) to fit the OGTT fasting index (score) to Ln(FFA AUC * C-peptide AUC). The coefficient of determination, denoted $R^2$ indicates how well the data fit the statistical model. Typically, $R^2$ of below 0.3 indicates a weak fitting, $R^2$ of above 0.5 indicates a moderate fitting, $R^2$ of above 0.7 indicates a strong fitting, and $R^2$ of above 0.8 indicates a very strong fitting. Bootstrapping method was used for internal validation, which produced 10,000 random samples of the cohort, wherein the distribution of the parameter estimates were used for likely optimum ranges. Here, estimates for the median values of each parameter distribution were obtained as exponent of each biomarker in the algorithms.

Next, the OGTT fasting index (score) was calculated for all subjects based on the developed algorithm, using the median value of each parameter distribution, to predict impaired glucose tolerance (IGT). The OGTT fasting index was also calculated by additionally including as a covariate to predict impaired glucose tolerance (IGT), i.e. the score for predicting 2-hour glucose ≥140 mg/dL was adjusted for factors such as age, sex, BMI, and fasting glucose. Additional factors, HbA1c and fasting insulin, were added to the list of covariates. Multivariable logistic regression was used to test the association, discrimination, calibration, and reclassification of patients using the new OGTT fasting index including the above list of confounding variables.

Residual diagnostics were conducted to verify model assumptions and to assess influence of outlier and leverage data; and natural logarithm transformations improved model assumptions. SAS® software version 9.3 (SAS Institute Inc., Cary, N.C.) was used for all analyses.

Example 2

Predicting the Likelihood of Impaired Glucose Tolerance (IGT) Through Combining the Biomarkers of Free Fatty Acid (FFA), C-Peptide, Alpha Hydroxybutyrate (AHB), Ferritin, Linoleoyl-GPC (LGPC), and Adiponectin In this example, the OGTT fasting score was calculated combining the measured values for free fatty acid [mmol/L], C-peptide [ng/mL], alpha hydroxybutyrate [µg/mL], ferritin [ng/mL], linoleoyl-GPC [µg/mL], and adiponectin [µg/mL] from a patient sample.

The samples had previously been analyzed for the values of the area under the curve (AUC) for C-peptide and free fatty acid respectively, which, when multiplied together, strongly correlated with the IGT determined by a 2-hour OGTT.

The score was calculated according to the following equation (version 1):

$$Ln\left[\frac{FFA^{0.774} * Cpeptide^{0.679} * AHB^{0.0655} * Ferritin^{0.0407}}{LGPC^{0.0848} * Adiponectin^{0.131}}\right]$$

In the equation, the symbols and units of the measured levels are shown as below: Ln=natural logarithm; FFA=free fatty acid [mmol/L]; C-peptide [ng/mL]; AHB=alpha hydroxybutyrate [µg/mL]; Ferritin [ng/mL]; LGPC=Linoleoyl-GPC [µg/mL]; and Adiponectin [µg/mL].

As described in the Statistical Model in Example 1, the exponents for individual biomarkers in the above equation were derived from fitting the above equation to Ln(FFA AUC * C-peptide AUC) multiple linear regression, and a population study of 10,000 bootstrapped samples, as shown in Table 2. FIG. 1 shows the histogram of an OGTT fasting score distribution from patients of a population study using Version 1 of the equation. As can be seen in the figure, the score distributions (using version 1 of the equation) from the population study (kernel) is close to a normal distribution (normal).

TABLE 2

Fitting version 1 equation to predict Ln(FFA AUC * C-peptide AUC), wherein $R^2$ = 0.819, Adjusted $R^2$ = 0.814. Distribution of the biomarkers parameters from 10,000 bootstrapped samples.

| Variable | Mean Estimate | Standard Deviation | Estimated Percentiles | | |
|---|---|---|---|---|---|
| | | | 5% | Median | 95% |
| Intercept | 2.461826 | 0.183307 | 2.161635 | 2.458463 | 2.767679 |
| Ln(FFA) | 0.775629 | 0.051077 | 0.693763 | 0.774240 | 0.861140 |
| Ln(C-peptide) | 0.679731 | 0.045375 | 0.605560 | 0.679254 | 0.754894 |
| Ln(AHB) | 0.065374 | 0.050073 | −0.017530 | 0.065488 | 0.148606 |
| Ln(Ferritin) | 0.040470 | 0.018123 | 0.010119 | 0.040689 | 0.069297 |
| Ln(LGPC) | −0.084848 | 0.041948 | −0.153274 | −0.084788 | −0.016521 |
| Ln(Adiponectin) | −0.130906 | 0.026055 | −0.173755 | −0.130827 | −0.087847 |

Estimates for the median values (with 3-digit accuracy) were used in the above equation.

Example 3

Predicting the Likelihood of Impaired Glucose Tolerance (IGT) Through Combining the Biomarkers of Free Fatty Acid (FFA), C-Peptide, and Adiponectin In this example, the OGTT fasting score was calculated combining the measured values for FFA=free fatty acid [mmol/L], C-peptide [ng/mL], and adiponectin [µg/mL] from a patient sample.

The samples had previously been analyzed for the values of the area under the curve (AUC) for C-peptide and free fatty acid respectively, which, when multiplied together, strongly correlate with the IGT determined by a 2-hour OGTT.

The score was calculated according to the following equation (version 2):

$$Ln\left[\frac{FFA^{0.825} * Cpeptide^{0.729}}{Adiponectin^{0.137}}\right].$$

Figure 2:
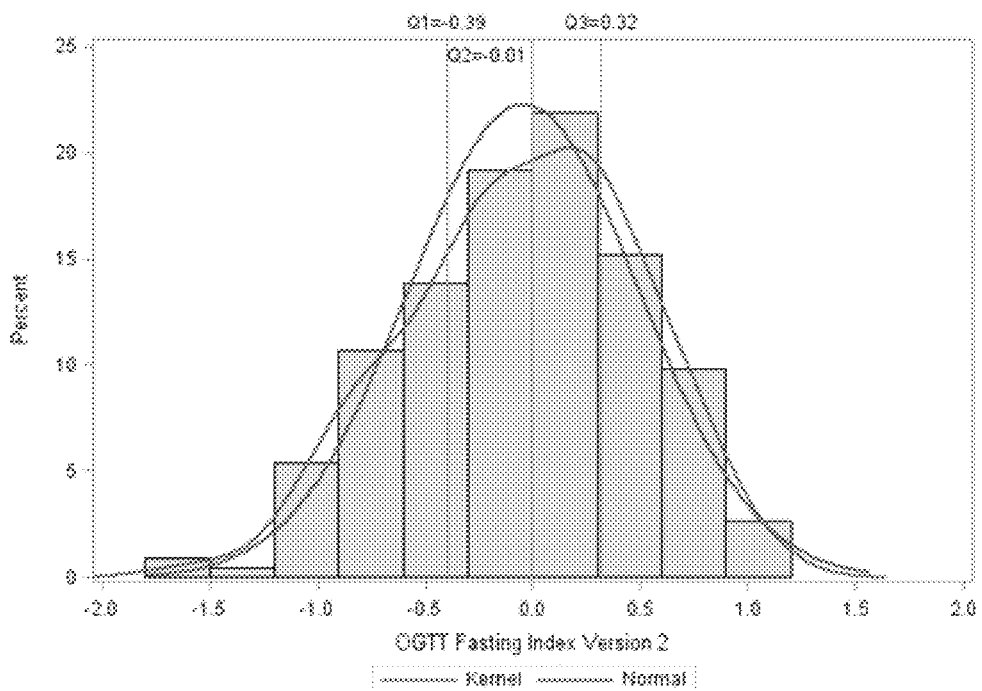
FIG. 2 is a graph showing the histogram of a OGTT fasting score distribution from patients of a population study using Version 2 of the equation. The vertical lines of Q1, Q2, and Q3 indicate the score cutoffs for the first quantile, the second quantile, and the third quantile, respectively. The line "kernel" represents the kernel density estimation, i.e., a non-parametric estimation of the probability density function of a random variable; and the line "normal" represents the best fit of the normal distribution.

As described in the Statistical Model in Example 1, the exponents for individual biomarkers in the above equation were derived from fitting the above equation to Ln(FFA AUC * C-peptide AUC) by multiple linear regression, and a population study of 10,000 bootstrapped samples, as shown in Table 3. FIG. 2 shows the histogram of an OGTT fasting score distribution from patients of a population study using Version 2 of the equation. As can be seen in the figure, the score distributions (using version 2 of the equation) from the population study (kernel) is close to a normal distribution (normal).

TABLE 3

Fitting version 1 equation to predict Ln(FFA AUC * C-peptide AUC), wherein $R^2$ = 0.810, Adjusted $R^2$ = 0.807. Distribution of the biomarkers parameters from 10,000 bootstrapped samples.

| Variable | Mean Estimate | Standard Deviation | Estimated Percentiles | | |
|---|---|---|---|---|---|
| | | | 5% | Median | 95% |
| Intercept | 2.491246 | 0.097410 | 2.332730 | 2.489855 | 2.652964 |
| Ln(FFA) | 0.825568 | 0.043703 | 0.754274 | 0.825499 | 0.897544 |
| Ln(C-peptide) | 0.729159 | 0.041904 | 0.660306 | 0.729303 | 0.797486 |
| Ln(Adiponectin) | −0.136944 | 0.025930 | −0.179457 | −0.136691 | −0.094451 |

Estimates for the median values (with 3-digit accuracy) were used in the above equation.

Example 4

Predicting the Likelihood of Impaired Glucose Tolerance (IGT) Through Combining the Biomarkers of Free Fatty Acid (FFA), C-Peptide, Ferritin, Linoleoyl-GPC (LGPC), and Adiponectin In this example, the OGTT fasting score was calculated combining the measured values for FFA=free fatty acid [mmol/L], C-peptide [ng/mL], ferritin [ng/mL], LGPC=linoleoyl-GPC [µg/mL], and adiponectin [µg/mL] from a patient sample.

The samples had previously been analyzed for the values of the area under the curve (AUC) for C-peptide and free fatty acid respectively, which, when multiplied together, strongly correlate with IGT determined by a 2-hour OGTT.

The score was calculated according to the following equation (version 3):

$$Ln\left[\frac{FFA^{0.807} * Cpeptide^{0.688} * Ferritin^{0.0447}}{LGPC^{0.0852} * Adiponectin^{0.130}}\right].$$

As described in the Statistical Model in Example 1, the exponents for individual biomarkers in the above equation were derived from fitting the above equation to Ln(FFA AUC * C-peptide AUC) by multiple linear regression, and a population study of 10,000 bootstrapped samples, as shown in Table 4. The histogram of an OGTT fasting score distribution (not shown) demonstrated a distribution that closely represented a normal distribution similar to FIGS. 1 and 2.

TABLE 4

Fitting version 3 equation to predict Ln(FFA AUC * C-peptide AUC), wherein $R^2$ = 0.817, Adjusted $R^2$ = 0.813. Distribution of the biomarkers parameters from 10,000 bootstrapped samples.

| Variable | Mean Estimate | Standard Deviation | Estimated Percentiles | | |
|---|---|---|---|---|---|
| | | | 5% | Median | 95% |
| Intercept | 2.551320 | 0.167395 | 2.281722 | 2.547731 | 2.829960 |
| Ln(FFA) | 0.806810 | 0.043341 | 0.735948 | 0.806970 | 0.877515 |
| Ln(C-peptide) | 0.688440 | 0.044009 | 0.616929 | 0.687867 | 0.761727 |
| Ln(Ferritin) | 0.044726 | 0.017969 | 0.015035 | 0.044679 | 0.074137 |
| Ln(LGPC) | −0.085481 | 0.041582 | −0.154422 | −0.085184 | −0.017059 |
| Ln(Adiponectin) | −0.129678 | 0.026359 | −0.172927 | −0.129781 | −0.086016 |

Estimates for the median values (with 3-digit accuracy) were used in the above equation.

Table 5 shows the odds ratios and AUC (c-statistics) derived using each of the three illustrative exemplary algorithms (Versions 1-3) described in Examples 2-4, as compared to the odds ratios derived from the base model, and the odds ratios derived from combining the base model and each illustrative algorithm (Versions 1, 2, 3, respectively). The interpretation is that for every increase of the algorithm score of 1 SD, the odds of a subject having IGT increase by a given amount. For instance, in column 2 of Table 5, the odds ratio for version 1 of the algorithm (shown in Example 2) is 3.57, indicating that on a continuous scale, each increase in the algorithm score by 1 SD above the mean results in a patient being 3.57 times more likely to have IGT.

TABLE 5

T Prevalence (i.e., OGTT 2-hour glucose level ≥140 mg/dL)

| Model | Odds Ratio per 1 SD | | Discrimination | | | Integrated Discrimination | | | | | Continuous Net Reclassification Improvement | | | |
|---|---|---|---|---|---|---|---|---|---|---|---|---|---|---|
| | | | c-stat = | | | Hosmer-Lemeshow | Improvement | | | | % | | % | |
| | Est. | P-value | AUC | Δ | P-value | Calibration P-value | Δ Sens | P-value | Δ Spec | P-value | IGT | P-value | No IGT | P-value |
| Base* | — | — | 0.763 | — | — | 0.19 | — | — | — | — | — | — | — | — |
| V1 Alone | 3.57 | <0.0001 | 0.775 | — | — | 0.18 | — | — | — | — | — | — | — | — |
| V2 Alone | 3.39 | <0.0001 | 0.764 | — | — | 0.97 | — | — | — | — | — | — | — | — |
| V3 Alone | 3.59 | <0.0001 | 0.774 | — | — | 0.69 | — | — | — | — | — | — | — | — |
| Base + V1 | 2.84 | 0.0001 | 0.820 | 0.058 | 0.0072 | 0.65 | 0.048 | 0.0099 | 0.017 | 0.046 | 44% | 0.0009 | 19% | 0.018 |
| Base + V2 | 2.68 | 0.0003 | 0.815 | 0.052 | 0.0098 | 0.60 | 0.044 | 0.014 | 0.015 | 0.059 | 40% | 0.0023 | 16% | 0.041 |
| Base + V3 | 2.90 | 0.0001 | 0.821 | 0.058 | 0.0066 | 0.90 | 0.050 | 0.0081 | 0.018 | 0.042 | 40% | 0.0023 | 21% | 0.0076 |

*Base Model: age, sex, BMI, Lu(fasting glucose); In the base model only Ln(fasting glucose) was significant (p < 0.0001), other variables (minimum p = 0.14).

Moreover, as shown in Table 5 and FIGS. 3-5, combining the score obtained from step b) of the method with the base model score provides an improved likelihood prediction than the base model score alone: the c-statistics (AUC) for the scores combining each equation with the base model were significantly greater than the base model alone. Surprisingly, the algorithm alone provides an improved likelihood prediction than the base model. As shown in Table 5, the c-statistics (AUC) for the scores from each equation alone were greater than the base model.

Example 5

Predicting the Likelihood of Impaired Glucose Tolerance (IGT) Through Combining the Biomarkers of Free Fatty Acid (FFA), Glucose, Myeloperoxidase (MPO), and Linoleoyl-GPC (LGPC)

In this example, the OGTT fasting score was calculated combining the measured values for free fatty acid [mmol/L], glucose [mg/dL], myeloperoxidase [pmol/L], and Linoleoyl-GPC [μg/mL] from a patient sample.

The samples had previously been analyzed for the values of the area under the curve (AUC) for C-peptide and free fatty acid respectively, which when multiplied together strongly correlated with the IGT determined by a 2-hour OGTT.

The score was calculated according to the following equation (version 4):

$$\text{Ln}\left[\frac{FFA^{1.838} * Glucose^{6.386} * MPO^{2.001}}{LGPC^{1.432}}\right].$$

In the equation, the symbols and units of the measured levels are shown as below: Ln=natural logarithm; FFA=free fatty acid [mmol/L]; Glucose [mg/dL]; MPO=Myeloperoxidase [pmol/L]; and LGPC=Linoleoyl-GPC [μg/mL].

Table 6 shows the odds ratios and AUC (c-statistics) derived from the exemplary algorithm (version 4) described in this example, as compared to the odds ratios derived from the base model (Model 1), and the odds ratios derived from combining the base model and version 4 algorithm. As shown in Table 6, combining the score obtained from step b) of the method with the base model score provides an improved likelihood prediction than the base model score alone: the c-statistics (AUC) for the scores combining version 4 equation with the base model was significantly greater than the base model alone. Surprisingly, the algorithm alone provides an improved likelihood prediction than the base model. As shown in Table 6, the c-statistics (AUC) for the score from version 4 equation was significantly greater than the base model.

TABLE 6

Predict IGT Prevalence, i.e. OGTT 2-hr glucose ≥140 mg/dL (N = 352 with 63 events)

| Model | Odds Ratio per 1 SD Est. (95% CI) | P-value | Discrimination c-stat = AUC | Δ | P-value | Hosmer-Lemeshow Calibration P-value | Integrated Discrimination Improvement Δ Sens | P-value | Δ Spec | P-value | Continuous Net Reclassification Improvement % IGT | P-value | % No IGT | P-value |
|---|---|---|---|---|---|---|---|---|---|---|---|---|---|---|
| Model 1* | — | — | 0.786 | — | — | 0.15 | — | — | — | — | — | — | — | — |
| Version 4 | 6.56 (4.03 to 10.7) | <0.0001 | 0.860 | — | — | 0.28 | — | — | — | — | — | — | — | — |
| Model 1 + version 4 | 8.07 (3.95 to 16.5) | <0.0001 | 0.876 | 0.090 | 0.0001 | 0.13 | 0.103 | <0.0001 | 0.022 | 0.0017 | 52% | <0.0001 | 45% | <0.0001 |

*Model 1: age, sex, BMI, log(fasting glucose), log(HbA1c), log(fasting insulin)

TABLE 7

Odds Ratio for IGT by Quartile of Version 4 OGTT Fasting Index

| | | 95% Confidence Interval | | |
|---|---|---|---|---|
| | Est. | Lower | Upper | P-value |
| 1$^{st}$ Quartile - Reference | 1.00 | — | — | — |
| 2$^{nd}$ Quartile vs 1$^{st}$ | 5.24 | 0.60 | 45.7 | 0.13 |
| 3$^{rd}$ Quartile vs 1$^{st}$ | 17.9 | 2.31 | 138.4 | 0.0058 |
| 4$^{th}$ Quartile vs 1$^{st}$ | 79.4 | 10.6 | 594.9 | <0.0001 |

Example 6

Predicting the Likelihood of Impaired Glucose Tolerance (IGT) Through Combining the Biomarkers of Free Fatty Acid (FFA), Glucose, Myeloperoxidase (MPO), Insulin, Fibrinogen, and Leptin In this example, the OGTT fasting score was calculated combining the measured values for free fatty acid [mmol/L], glucose [mg/dL], myeloperoxidase [pmol/L], insulin [µU/mL], fibrinogen [mg/dL], and leptin [ng/mL] from a patient sample.

The samples had previously been analyzed for the values of the area under the curve (AUC) for C-peptide and free fatty acid respectively, which when multiplied together strongly correlated with the IGT determined by a 2-hour OGTT.

The score was calculated according to the following equation (version 5):

$$Ln\left[\frac{FFA^{2.374} * Glucose^{5.248} * MPO^{1.741} * Insulin^{1.037} * Fibrinogen^{3.037}}{Leptin^{0.601}}\right]$$

In the equation, the symbols and units of the measured levels are shown as below: Ln=natural logarithm; FFA=free fatty acid [mmol/L]; Glucose [mg/dL]; MPO=Myeloperoxidase [pmol/L]; Insulin [µU/mL]; Fibrinogen [mg/dL]; and Leptin [ng/mL].

Table 8 summarizes the odds ratios and AUC (c-statistics) derived using each of the five illustrative exemplary algorithms (Versions 1-5) described in Examples 2-6, as compared to the odds ratios derived from the base model, and the odds ratios derived from combining the base model and each illustrative algorithm (Version 1, 2, 3, 4, 5, respectively). As shown in Table 8, combining the score obtained from step b) of the method with the base model score provides an improved likelihood prediction than the base model score alone: the c-statistics (AUC) for the scores combining each equation with the base model were significantly greater than the base model alone. Surprisingly, the algorithm alone provides an improved likelihood prediction than the base model. As shown in Table 8, the c-statistics (AUC) for the scores from each equation alone were greater than the base model.

TABLE 8

Predict IGT Prevalence, i.e. OGTT 2-hr glucose ≥140 mg/dL (N = 352 with 63 events)

| Model | Odds Ratio per 1 SD Est. | P-value | Discrimination c-stat = AUC | Δ | P-value | Hosmer-Lemeshow Calibration P-value | Integrated Discrimination Improvement Δ Sens | P-value | Δ Spec | P-value | Continuous Net Reclassification Improvement % IGT | P-value | % No IGT | P-value |
|---|---|---|---|---|---|---|---|---|---|---|---|---|---|---|
| Base** | — | — | 0.785 | — | — | 0.15 | — | — | — | — | — | — | — | — |
| V1 Alone | 4.03 | <0.0001 | 0.811 | — | — | 0.19 | — | — | — | — | — | — | — | — |
| V2 Alone | 3.78 | <0.0001 | 0.799 | — | — | 0.43 | — | — | — | — | — | — | — | — |
| V3 Alone | 4.01 | <0.0001 | 0.807 | — | — | 0.30 | — | — | — | — | — | — | — | — |
| V4 Alone | 6.71 | <0.0001 | 0.860 | — | — | 0.28 | — | — | — | — | — | — | — | — |
| V5 Alone | 7.94 | <0.0001 | 0.881 | — | — | 0.12 | — | — | — | — | — | — | — | — |
| Base + V1 | 3.05 | <0.0001 | 0.839 | 0.054 | 0.010 | 0.93 | | | | | | | | |
| Base + V2 | 2.74 | 0.0001 | 0.830 | 0.044 | 0.018 | 0.59 | | | | | | | | |

TABLE 8-continued

Predict IGT Prevalence, i.e. OGTT 2-hr glucose ≥140 mg/dL (N = 352 with 63 events)

| Model | Odds Ratio per 1 SD | | Discrimination | | | Hosmer-Lemeshow Calibration | Integrated Discrimination Improvement | | | | Continuous Net Reclassification Improvement | | | |
|---|---|---|---|---|---|---|---|---|---|---|---|---|---|---|
| | Est. | P-value | c-stat = AUC | Δ | P-value | P-value | Δ Sens | P-value | Δ Spec | P-value | IGT % | P-value | No IGT % | P-value |
| Base + V3 | 3.05 | <0.0001 | 0.838 | 0.053 | 0.0097 | 0.70 | | | | | | | | |
| Base + V4 | 8.07 | <0.0001 | 0.876 | 0.091 | 0.0001 | 0.13 | | | | | | | | |
| Base + V5 | 8.38 | <0.0001 | 0.886 | 0.101 | <0.0001 | 0.25 | | | | | | | | |

**Base Model: age, sex, BMI, log(fasting glucose), log(HbA1c), log(insulin)

What is claimed is:

1. A method of treating and/or preventing diabetes or a related cardio-diabetes condition and comorbidity in a subject, comprising: administering to the subject a drug or supplement in an amount effective to treat diabetes or the related cardio-diabetes condition and comorbidity, wherein the subject has been determined to have abnormal glucose tolerance or to be at risk for developing abnormal glucose tolerance by:
   a) obtaining a biological sample from the subject;
   b) processing the biological sample by one of the following:
      i) concentrating the biological sample to obtain a concentrated biological sample;
      ii) fractionating the biological sample to obtain a fractionated biological sample; or
      iii) separating the biological sample to obtain a separated biological sample;
   c) obtaining, from the concentrated biological sample, the fractionated biological sample, or the separated biological sample, a measured level of a combination of biomarkers selected from the group consisting of, free fatty acids, glucose, myeloperoxidase, insulin, fibrinogen, and leptin, that predict and/or provide information about at least three physiological processes selected from the group consisting of, adipose tissue insulin resistance, pancreatic beta cell dysfunction and/or exhaustion, muscle and/or hepatic insulin resistance, functional enhancement of insulin secretion by beta cells, inhibition of beta cell function, adipokine function, total glycemic control, and inflammation,
   d) calculating a score based on the measured levels of the combination of biomarkers, wherein the score calculation comprises:

$$\ln\left[\frac{FFA^{2.374} \times Glucose^{5.248} \times MPO^{1.7415} \times Insulin^{1.037} \times Fibrinogen^{3.037}}{Leptin^{0.601}}\right]$$

e) comparing the score to reference values from a population of randomly chosen subjects, with or without normal glucose tolerance, and
   f) identifying the subject as likely to develop abnormal glucose tolerance if the calculated score is elevated, wherein an elevated score correlates with an increased likelihood of elevation of blood glucose to ≥140 mg/dL at 2 hours after oral glucose tolerance test.

2. The method of claim 1, wherein the likelihood can be predicted by a single measurement of a single fasting sample.

3. The method of claim 1, wherein the score replaces the oral glucose tolerance test (OGTT) to predict likelihood of the subject having abnormal glucose tolerance.

4. The method of claim 1, wherein at least one of the biomarkers of the combination of biomarkers is a protein in a form of a monomer, a multimer, a complex with one or more other organic molecules, a normal (wild-type) form, a genetic variant with altered amino acid sequence or conformation, an isoform, a glycoform, a post-translationally modified form, an oxidized form, a form with altered biological function, a fragment/product of enzymatic cleavage, or an adduct with another chemical moiety.

5. The method of claim 1, wherein at least one of the biomarkers of the combination of biomarkers predicts and/or provides information about adipose tissue insulin resistance, and wherein the at least one biomarker that predicts and/or provides information about adipose tissue insulin resistance is a total free fatty acid or a component fatty acid species of a total free fatty acid.

6. The method of claim 1, wherein the mathematical transformation comprises:
   i) multiplying the measured level of each biomarker of the combination of biomarkers by a pre-determined exponent;
   ii) multiplying the products of the exponentiation generated from step i); and
   iii) logarithmically transforming the multiplied product generated from step ii).

7. The method of claim 1, further comprising:
   obtaining values for one or more base model factors selected from the group consisting of age, sex, body mass index (BMI), and fasting glucose, to predict the likelihood of the subject having abnormal glucose tolerance;
   calculating a based model score for the subject based on one or more values of the base model factors; and
   combining the score obtained from step b) with the calculated base model score, wherein the combined score is compared to reference values from a population.

8. The method of claim 7, wherein the base model factor is fasting glucose, and wherein the base model score is calculated by logarithmically transforming a measured level of fasting glucose in the subject.

9. The method of claim 7, wherein the combining the score obtained from step b) with the base model score provides an improved likelihood prediction than the base model score alone.

10. The method of claim 7, wherein the combining the score obtained from step b) with the base model score causes a net reclassification improvement (NRI) of the subject from having normal glucose tolerance (NGT) to impaired glucose tolerance (IGT), or from having MT to NGT.

11. The method of claim 10, wherein the NRI is at least about 10%.

12. The method of claim 1, further comprising monitoring the levels of the biomarkers in the subject to assess progression, improvement, normalization, and/or treatment efficacy, wherein the monitoring step comprises repeating steps a)-c) based on the levels of the combination of biomarkers from a biological sample in the subject obtained at a later time.

\* \* \* \* \*